(12) United States Patent  
Taylor et al.

(10) Patent No.: US 7,271,728 B2  
(45) Date of Patent: Sep. 18, 2007

(54) METHOD FOR ASSESSING IMPROVEMENT IN HAND HYGIENE PRACTICES

(75) Inventors: Patricia A. Taylor, New Philadelphia, OH (US); Brian G. Whitaker, Stow, OH (US)

(73) Assignee: GOJO Industries, Inc., Akron, OH (US)

( * ) Notice: Subject to any disclaimer, the term of this patent is extended or adjusted under 35 U.S.C. 154(b) by 198 days.

(21) Appl. No.: 11/152,474

(22) Filed: Jun. 13, 2005

(65) Prior Publication Data

US 2007/0008146 A1    Jan. 11, 2007

(51) Int. Cl.
G08B 23/00    (2006.01)

(52) U.S. Cl. .............. 340/573.1; 340/539.12; 4/623

(58) Field of Classification Search .......... 340/573.1, 340/545, 691, 603, 539.11, 539.12, 545.1, 340/691.1; 222/52, 185.1; 137/551; 4/623; 702/176

See application file for complete search history.

(56) References Cited

U.S. PATENT DOCUMENTS

| | | | | |
|---|---|---|---|---|
| 5,202,666 A | * | 4/1993 | Knippscheer | 340/573.1 |
| 5,939,974 A | * | 8/1999 | Heagle et al. | 340/286.09 |
| 5,945,910 A | * | 8/1999 | Gorra | 340/573.1 |
| 6,125,482 A | * | 10/2000 | Foster | 4/623 |
| 6,236,317 B1 | * | 5/2001 | Cohen et al. | 340/573.1 |
| 6,392,546 B1 | * | 5/2002 | Smith | 340/573.1 |
| 6,426,701 B1 | * | 7/2002 | Levy et al. | 340/573.1 |
| 6,882,278 B2 | * | 4/2005 | Winings et al. | 340/573.1 |
| 6,975,231 B2 | * | 12/2005 | Lane et al. | 340/573.1 |
| 2004/0090333 A1 | * | 5/2004 | Wildman et al. | 340/573.1 |

* cited by examiner

Primary Examiner—Brent A. Swarthout
(74) Attorney, Agent, or Firm—Renner, Kenner, Greive, Bobak, Taylor & Weber

(57) ABSTRACT

A method for assessing improvement in hand hygiene practices using sanitation solution dispensers deployed within particular areas of interest in a healthcare facility or the like. Each of the dispensers has a counter associated therewith, with the counter producing a count indicative of actual events of a healthcare worker sanitizing his/her hands. Other data is acquired that impacts the number of anticipated hand sanitation events in this particular area of interest. From this data, a number of anticipated hand sanitation events is determined. Finally, a determination is made, from information obtained through actual observation, of the number of opportunities that healthcare workers will have for hand sanitation in the area of interest over a particular period of time. A performance index, indicative of compliance with hand hygiene protocol, is then obtained by dividing the difference between the actual number of hand sanitizing events and the number of anticipated hand hygiene events by the number of opportunities for such hand hygiene events. This index may then be used to gauge improvement or regression in hand hygiene practices in an area of interest, or to measure the effectiveness of intervention programs, or to compare performance between various areas of interest.

11 Claims, 2 Drawing Sheets

METHOD FOR ASSESSING IMPROVEMENT IN HAND HYGIENE PRACTICES

TECHNICAL FIELD

The invention herein resides in the art of hand hygiene and, more particularly, relates to methods for assessing improvement in hand hygiene practices. More specifically, the invention relates to a methodology by which hand hygiene practices in a facility may be benchmarked and assessed for improvement over time, which allows for the evaluation of the efficacy of intervention programs regarding hand hygiene.

BACKGROUND ART

Good hand hygiene practices are a requisite for good health. While personal hand hygiene practices may directly impact the health of an individual, the corporate or institutional practices of individuals associated therewith may greatly impact the health of multitudes of others. It is well known that disease and infection is often communicated from one person to another as a consequence of poor hand hygiene practices by one or more persons in a chain of contact. In the hospitality industry, where employees have contact with food, service ware, bedding and the public, the possibilities for transmitting germs from one person to another are great. Schools, daycare centers, and offices have similar issues. But, the issue is probably most pronounced in the healthcare industry itself.

It is presently believed that hospital acquired infections cause approximately 90,000 deaths per year and nearly one third of these, or 30,000 deaths, are attributable to poor hand hygiene. Indeed, the Centers for Disease Control recognizes improved hand hygiene as a key to substantially reducing hospital or healthcare acquired infections.

The failure of workers to employ good hand hygiene practices and to comply with standards for hand hygiene results from opposition based in apathy, time pressures, resistance to change and the like. Indeed, there are many excuses for the failure to comply with hand hygiene norms in many key industries and, while the healthcare industry will be primarily addressed herein, it will be understood that the problems and resultant solutions presented are applicable to multiple industries and service organizations.

While the need for good hand hygiene has been well known and documented in the past, there has been a egregious failure to develop and sustain improvement. Indeed, it has been extremely difficult in the past to even assess the level of hand hygiene compliance within an institution such as a hospital or the like. Compliance has typically been defined as the number of opportunities that an employee or group of employees have had to wash or sanitize their hands, divided by the number of times that such employee or employees actually did wash or sanitize their hands. In the past, the assessment of compliance has been undertaken by physical observation, by the posting of individuals, cameras or the like throughout a facility to monitor the activities of the employees. In such a system a count is actually made of the number of opportunities that the workers had to wash or sanitize their hands, as well as the number of times that the opportunities were engaged by actual hand washing or sanitizing.

The physical monitoring of hand washing opportunities and hand washing events in the marketplace has been found to be given to significant inaccuracies. Employees who know they are being monitored more often seize the opportunity to sanitize their hands, when they would not have done so absent the knowledge that they were being monitored. Moreover, it has been found that observers occasionally demonstrate bias toward workers or groups of workers. Consequently, it has been found that physical observations tend to skew the count of handwash events actually undertaken by the employees. Further, personal observations within a healthcare or other work facility have typically been found to be intimidating and offensive.

While actual observations have been found to skew the count of handwash events, that technique has been determined to provide a reasonably accurate measure of handwash opportunities within the facility. Indeed, the literature is replete with published reports of handwash opportunities for various healthcare facilities, divisions and subdivisions within hospitals and the like. As matters now stand, information is available for assessing the number of handwash opportunities that present themselves in various healthcare environments, that information having been obtained from actual observation. Accordingly, by extrapolation and further assessment and analysis, it is possible to predict the number of handwash opportunities that will present themselves in a broad range of healthcare environments within a hospital, nursing home, or the like.

However, there remains a need in the art for the provision of a methodology by which hand hygiene compliance can be determined and that will not disrupt or disturb the environment of the hospital or healthcare facility, which will be discrete and non-threatening to healthcare workers to the extent that employment of the methodology within a hospital or the like is transparent to the healthcare workers, and which is easy to use and employ with state of the art and presently existing hand sanitation dispensers employed within the hospital. There is further a need for a methodology by which hand hygiene compliance can be monitored and assessed which is capable of generating a performance index to allow for comparisons between healthcare facilities, wards, divisions, and subdivisions of a similar nature, and which allows for bench marking to allow an analysis of the efficacy of intervention programs. All of this is most desirable while complying with standards set by various governmental agencies such as Centers for Disease Control and Prevention ("CDC"), Joint Commission on Accrediting Healthcare Organizations ("JCAHO"), and Centers for Medicaid and Medicare Services ("CMS").

DISCLOSURE OF THE INVENTION

In light of the foregoing, it is a first aspect of the invention to provide a method for assessing improvement in hand hygiene practices that is substantially transparent to the operation of hospitals and other healthcare facilities.

Another aspect of the invention is the provision of a method for assessing improvement in hand hygiene practices that is neither intimidating nor offensive to healthcare workers.

Still a further aspect of the invention is the provision of a method for assessing improvement in hand hygiene practices that compares or rates the performance of one healthcare facility, division of subdivision with like facilities, divisions or subdivisions.

Still a further aspect of the invention is the provision of a method for assessing the improvement in hand hygiene practices that provides a means for bench marking performance to allow for assessment of the efficacy of intervention hand hygiene programs.

Still a further aspect of the invention is the provision of a method for assessing improvement in hand hygiene practices that meets CDC, JCAHO and CMS standards.

Yet a further aspect of the invention is the provision of a method for assessing improvement in hand hygiene practices that is easy to employ and cost effective when implemented with presently existing state of the art hand hygiene solution dispensers.

The foregoing and other aspect of the invention that will become apparent as the detailed description proceeds are achieved by a method for assessing improvement in hand hygiene practices in an area of interest, comprising: installing sanitation solution dispensers in the area of interest, said dispensers having counters associated therewith, said counters counting a first number of actual hand hygiene events; acquiring data impacting a number of anticipated hand hygiene events respecting the area of interest; deriving from said acquired data a second number of anticipated hand hygiene events for the area of interest; determining a third number of opportunities for hand hygiene events for the area of interest; and developing a performance index by dividing a difference between said first and second numbers by said third number.

Further aspects of the invention which will become apparent herein are achieved by a method for assessing improvement in hand hygiene practices in an area of interest, the area having hand washing or hand sanitizing solution dispensers therein, said dispensers having associated counters, comprising: obtaining from the counters a first number of actual hand hygiene events in the area of interest; acquiring data relevant to a second number of expected hand hygiene events in the area of interest; and calculating a difference between said first and second numbers, said difference correlating to a degree of performance between expected and actual hand hygiene events.

DESCRIPTION OF DRAWINGS

For a complete understanding of the objects, techniques and structure of the invention, reference should be made to the following detailed description and accompanying drawings wherein.

DETAILED DESCRIPTION OF PREFERRED EMBODIMENT FOR CARRYING OUT THE INVENTION

The instant invention provides a method for monitoring and assessing the compliance of healthcare workers with hand hygiene protocols. In the context of the invention, a hand hygiene event is one in which an alcohol-based or other suitable sanitizing liquid, gel or other hand washing solution is dispensed from a wall mounted or counter based unit into the hands of a healthcare worker and the solution is then rubbed over, into and about the hands of the worker to provide the desired sanitation. Such units and solutions are well known and commonly available in hospitals and other healthcare facilities, as well as other institutions where hand hygiene is of significant importance. While the invention herein will be discussed and described with respect to the healthcare industry, it is to be understood that it is applicable to other industries, as well.

While such dispensers and solutions are commonly known, they are not used with the frequency necessary to significantly reduce the transmittal of disease in healthcare facilities that are known to result from poor hand hygiene practices. While intervention programs have often been employed to encourage improved hand hygiene in such facilities, the efficacy of such programs is difficult to measure, as is the level of compliance of healthcare workers with hand hygiene protocols. As a consequence, the invention contemplates a system and method by which a determination can be made as to the number of hand hygiene ("hand wash") opportunities that are existent in the facility over a given period of time, and compare that with the number of hand hygiene ("handwash") events actually undertaken in order to assess a level of compliance with hand hygiene protocol. When dividing the events by the opportunities and multiplying by 100, an estimate of a percentage of compliance can be readily determined.

As presented above, it is appreciated that it is difficult to assess, with repeated accuracy, both the handwash events and opportunities. Accordingly, the invention contemplates relative assessments, where the methodology disclosed herein is repeatedly and consistently employed such that comparisons can be made against previously obtained evaluations at the same facility, or at other similar facilities employing the same methodology, to evaluate relative performance, degrees of improvement or regression, and the efficacy of any intervention programs. Accordingly, the invention does not contemplate the simplistic division of the number of events by the number of opportunities, but a more normalized approach as presented hereinafter.

Figure 1:
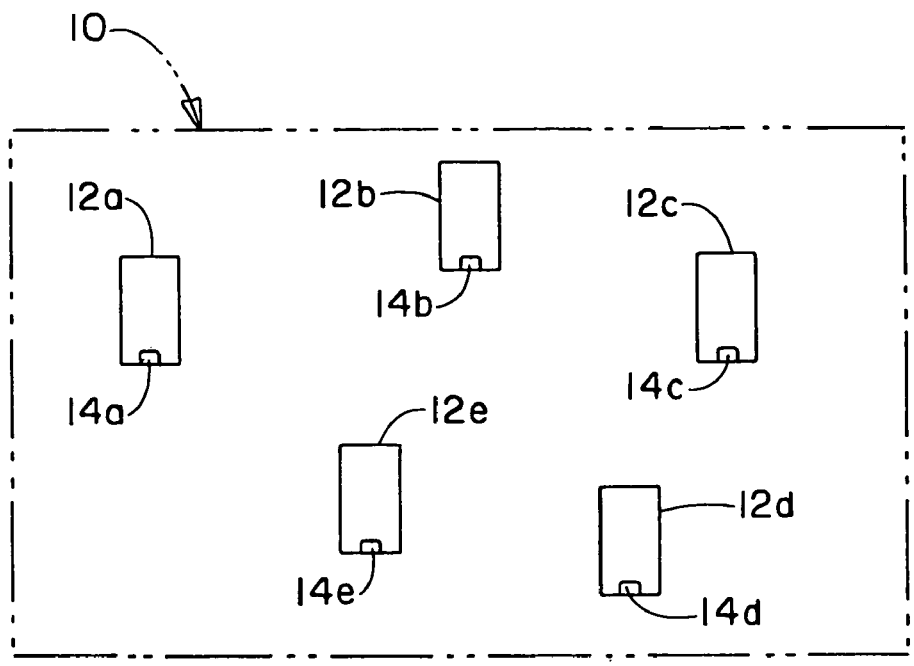
FIG. 1 is an illustration of the placement of hand hygiene solution dispensers positioned throughout a healthcare facility.

With reference now to the drawings, it can be seen in FIG. 1 that a specified area of a healthcare facility is designated generally by the numeral 10. For example, the area 10 may be a hospital as a whole, or a ward, division or subdivision thereof. Received within the area 10 and suitably mounted on walls, counters or the like, are a plurality of dispensers 12a-12e containing a suitable sanitizing liquid or gel, such an alcohol-based material. Each of the dispensers 12a-12e has a respectively associated actuator lever or button 14a-14e, allowing a healthcare worker or other individual to actuate the associated dispenser to dispense a predetermined amount of the sanitizing liquid or gel. Such dispensers and their actuation mechanisms are commonly known in the art and are typically mounted on a wall or a counter near a particular area where protocol suggests that a sanitizing or handwash event should occur. For example, such dispensers are often positioned in patient rooms, examining rooms, near nursing stations, and the like. The intent is that, before touching a patient, the healthcare worker should perform a sanitizing or handwash operation or event.

In accordance with the invention, it is assumed that the actuation of a dispenser 12 correlates with a hand hygiene event. In this regard, counters are employed with the dispensers 12 to count the number of dispensing operations, and thereby assess the number of handwash events. While it is understood that a healthcare worker may actuate a lever 14 several times in sequence to obtain what is perceived to be an adequate amount of sanitized liquid or gel, the counters associated with the dispensers 12 are conditioned and timed such that such a plurality of pushes on the lever are counted as but a single handwash event.

Figure 2:
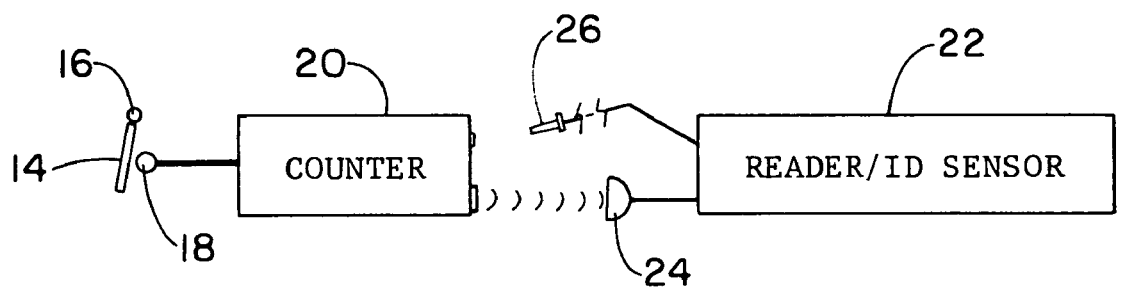
FIG. 2 is an illustration of a counter associated with the actuating mechanism of each of the dispensers of FIG. 1, and a reader/sensor capable of reading and resetting the various counters.

As shown in FIG. 2, each of the levers 14, pivotal about a pivot point 16, are interconnected through a contact or mechanical plunger 18 to increment a counter 20 uniquely associated with each dispenser. The counters 20 are adapted to be read either manually, in the event of a mechanical counter, or by means of an appropriate reader 22. The counter can be read by an infrared sensor 24, or a digital probe 26, as the case may be. The reader 22 also provides means for resetting the counter 20, if desired. The reader 22 also obtains from the counter 20 an identification of the associated dispenser 12a-12e, serving to identify the area 10 with which it is associated. Accordingly, on any desired periodic basis, the counters 20 maintained throughout the region or area 10 may be read and reset, providing data corresponding to the number of hand wash cycles undertaken at that dispenser in the period of time since the counters were last read. Accordingly, a rather accurate number of handwash events can be determined for any desired region 10.

The invention contemplates the development and employment of residual and performance indicies as a means for assessing and monitoring performance and improvement in hand hygiene compliance. In that regard, a residual index is generated by dividing the difference between actual handwash events and predicted handwash events by the number of handwash opportunities provided at a given location 10 over a given period of time. From the residual index, a performance index can be developed by simply augmenting the scale of the residual index. The technique for acquiring the data necessary for the generation of the indicies just described, and the use to which such indicies may be put, is set forth in detail below, with reference to FIG. 3.

Figure 3:
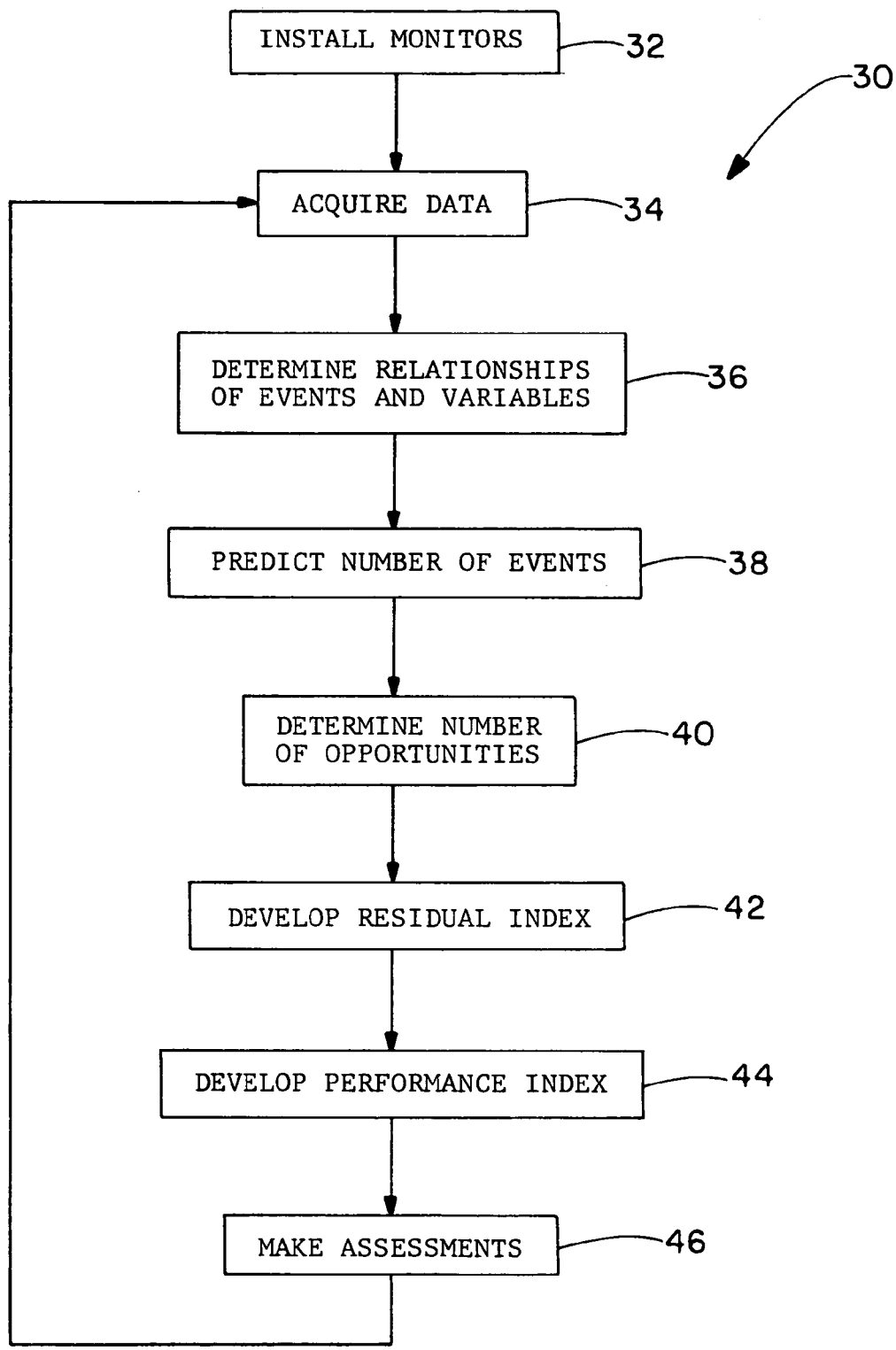
FIG. 3 is a block diagram showing a methodology of the invention.

Referring now to FIG. 3, it can be seen that a method for assessing improvement in hand hygiene practices is designated generally by the numeral 30. As a starting point, monitors or counters 20 are installed in each of the dispensers 12a-12e in a region 10 as set forth at 32. Next, at 34, a plurality of data is acquired regarding the region 10. The data acquired at 34 includes, but is not necessarily limited to, the actual handwash events determined by the counters 20 associated with the dispensers 12, along with various parameters that have been found to impact compliance. This data, unique to each area 10, includes the number of beds in the area, the occupancy rate of the area, the acuity rating of the area, the infection rate associated with the area 10, the period of time of interest, the number of staffing hours worked, and the like.

With the monitors installed at 32 and data acquired at 34, relationships can be developed at 36 between the number of handwash events undertaken in a given period of time as it relates to the variables of occupancy rates, number of beds, acuity rating, infection rates, number of hours worked, staffing hours, and the like. By employing standard multiple regression, the variables for which data was acquired at 34 can be assessed as to their impact on the number of actual handwash events as monitored at 32. With this information acquired over time, a determination may be made of the relationships of the handwash events with the variables, it being understood that in some regions 10 different variables will impact the number of handwash events than in other regions 10. In any event, with correlations being made as by standard multiple regression, it is possible to then predict for any region 10 the number of handwash events to be expected in any given period of time. This prediction is made at 38. Accordingly, there is now at hand the numerator of the formula referenced above for determining or establishing a residual or performance index. The actual number of handwash events can be monitored and a prediction of the number of events can be made.

At 40, the denominator of the formula for determining the performance index can be established. As presented above, the literature is replete with data indicating the number of handwash opportunities available in hospitals of various sizes and natures, as well as specific wards, divisions and subdivisions. These opportunities have been determined by actual observation, and it has been found that extrapolation can be made for any particular area 10 by taking into account the parameters of number of beds and hours observed.

At 42, a residual index can be generated by determining the difference between the actual handwash events determined at 32 from the counters 20 of the dispensers 12 and the predicted number of handwash events assessed at 38, and dividing that difference by the number of opportunities for handwash events as determined at 40. Accordingly, the residual index is generated at 42 and available for further use in assessment. It will be appreciated that if the predicted number of events is subtracted from the actual number of events for the numerator of the formula, an index of zero would represent substantially no change in performance, a negative index would indicate a shortfall, and a positive index would indicate an increase in performance. However, as cautioned above, the residual and performance indicies are generated for purposes of monitoring activities over a period of time to assess improvement or regression, and to assess the efficacy of intervention programs, not to provide an absolute measure of compliance.

The residual index 42 can be scaled to comprise a number between zero and 100, for example, eliminating negative numbers and providing a more normalized index that can be readily perceived and appreciated by healthcare workers. This normalization and development of a performance index is undertaken at 44. The performance index is basically a rescaled and rectified residual index obtained by rescaling or shifting the scale of the residual index.

With the residual or performance index at hand, various assessments can be made at 46. For example, by comparing the present index with previously obtained indicies, an assessment of improvement or regression can be made. In like manner, indicies developed in periods of time following an intervention program can be employed to assess the efficacy of the intervention program and/or any refreshers thereof. Further, with various institutions of similar size and nature, or wards, divisions or subdivisions of similar size and nature, participating in a program such as that set forth in FIG. 3, comparisons can be made between facilities, wards, and the like to assess relative degrees of compliance and how one facility "stacks up" against another similar facility.

As shown in FIG. 3, the process 30 is a continual process, looping back from 46 to the acquisition of data at 34 for continued verification of the criteria on which the number of events is predicted at 38 or the number of opportunities determined at 40. Accordingly, the process 30 is an adaptive process, given to adjustments, as required.

Those skilled in the art will appreciate that three primary data sources are required for the generation of the residual and performance indicies. The number of actual hand wash events is determined from the counters 20 of the dispensers 12 within the region 10 for the particular time period of interest. The predicted number of hand wash events is determined from what has previously actually been monitored by the counters 20 within the region 10, augmented by any changes in staffing, acuity, number of beds, infection rates, and the like. Finally, the denominator of the formula, the number of hand wash event opportunities, is developed from a retrospective study of the literature, providing data derived from actual observations, augmented only by the number of beds in the region 10 and the number of hours observed. Those skilled in the art will readily appreciate that if the indicies are used only to provide for an assessment of improvement or regression in performance, the denominator can actually be eliminated, and the residual and performance index can be generated by simply determining the difference between the number of predicted hand wash events and those actually counted. However, the denominator serves to normalize the indicies as a function of number of beds and period of time observed. Consequently, this normalization process allows for relative comparisons between facilities such that one facility can compare its performance to that of another similar facility, adjustments having been made for differences in bed size and/or period of observation. Since the denominator would typically remain constant for any given facility, it becomes unnecessary in the determination of the indicies if comparisons are only to be made against previously determined indicies for the same region 10.

Thus it can be seen that the various aspects of the invention have been satisfied by the structure and process presented above. While in accordance with the patent statutes only the best mode and preferred embodiment of the invention has been presented and described in detail, the invention is not limited thereto or thereby. Accordingly, for an appreciation of the scope and breadth of the invention reference should be made to the following claim.

What is claimed is:

1. A method for assessing improvement in hand hygiene practices in an area of interest, comprising:
    installing sanitation solution dispensers in the area of interest, said dispensers having counters associated therewith, said counters counting a first number of actual hand hygiene events;
    acquiring data impacting a number of anticipated hand hygiene events respecting the area of interest;
    deriving from said acquired data a second number of anticipated hand hygiene events for the area of interest;
    determining a third number of opportunities for hand hygiene events for the area of interest; and
    developing a performance index by dividing a difference between said first and second numbers by said third number.

2. The method as recited in claim 1, wherein said step of acquiring data impacting a number of anticipated hand hygiene events comprises acquiring data from among the group comprising the number of beds, occupancy rate, acuity rating and infection rate of the area of interest.

3. The method as recited in claim 2, wherein said step of deriving said second number of anticipated hand hygiene events further comprises assessing previously acquired said first numbers of actual hand hygiene events for said area of interest.

4. The method as recited in claim 2, wherein said step of determining said third number of opportunities comprises assessing data acquired from actual observation of such opportunities.

5. The method as recited in claim 4, wherein said step of determining said third number of opportunities comprises augmenting said assessed data as a function of a number of beds in said area of interest.

6. A method for assessing improvement in hand hygiene practices in an area of interest, the area having hand washing or hand sanitizing solution dispensers therein, said dispensers having associated counters, comprising:
    obtaining from the counters a first number of actual hand hygiene events in the area of interest, said second number being determined as a function of parameters comprising a number of beds in said area of interest;
    acquiring data relevant to a second number of expected hand hygiene events in the area of interest; and
    calculating a difference between said first and second numbers, said difference correlating to a degree of performance between expected and actual hand hygiene events.

7. The method according to claim 6, wherein said parameters further comprise an acuity rating of said area of interest.

8. The method according to claim 6, wherein said parameters further comprise an infection rate associated with said area of interest.

9. A method for assessing improvement in hand hygiene practices in an area of interest, the area having hand washing or hand sanitizing solution dispensers therein, said dispensers having associated counters, comprising:
    obtaining from the counters a first number of actual hand hygiene events in the area of interest;
    acquiring data relevant to a second number of expected hand hygiene events in the area of interest;
    calculating a difference between said first and second numbers, said difference correlating to a degree of performance between expected and actual hand hygiene events; and
    normalizing said difference as a function of a third number of opportunities for hand hygiene in said areas of interest.

10. The method according to claim 9, wherein said third member is derived from actual observation of opportunities for hand hygiene events, augmented as a function of a number of beds in said area of interest.

11. The method according to claim 10, wherein such difference is divided by said third member to effect said normalization.

* * * * *